United States Patent [19]

Hascoet et al.

[11] Patent Number: 5,480,417
[45] Date of Patent: * Jan. 2, 1996

[54] METHOD AND APPARATUS FOR THE SURGICAL TREATMENT OF TISSUES BY THERMAL EFFECT, AND IN PARTICULAR THE PROSTATE, USING A URETHRAL MICROWAVE-EMITTING PROBE MEANS

[75] Inventors: Gérard Hascoet, Paris; Francois LaCoste, Lyons; Muriel Cathaud, Venissieux; Jean-Marie Jacomino, Villeurbanne; Marian Devonec, Miribel; Paul Perrin, Lyons, all of France

[73] Assignee: Technomed Medical Systems, Vaulx-en-Velin, France

[*] Notice: The portion of the term of this patent subsequent to Aug. 10, 2010, has been disclaimed.

[21] Appl. No.: 66,774

[22] Filed: May 24, 1993

Related U.S. Application Data

[60] Division of Ser. No. 667,847, Mar. 12, 1991, Pat. No. 5,234,004, which is a continuation-in-part of Ser. No. 438,741, Nov. 17, 1989, abandoned.

[30] Foreign Application Priority Data

Nov. 21, 1988 [FR] France ................................. 88 15126
Mar. 12, 1990 [FR] France ................................. 90 03121

[51] Int. Cl.$^6$ .................................................. A61N 5/02
[52] U.S. Cl. .......................... 607/101; 607/102; 607/113; 607/116; 607/156
[58] Field of Search ...................... 128/736, 660.03; 607/101, 102, 113, 116, 156

[56] References Cited

U.S. PATENT DOCUMENTS

| | | |
|---|---|---|
| 3,154,077 | 10/1964 | Cannon . |
| 4,204,549 | 5/1980 | Paglione .................... 128/784 |
| 4,311,154 | 1/1982 | Sterzer et al. . |
| 4,612,940 | 9/1986 | Kasevich et al. ................ 128/804 |
| 4,662,383 | 5/1987 | Sogawa et al. . |
| 4,676,258 | 6/1987 | Inokuchi et al. ................ 128/804 |
| 4,700,716 | 10/1987 | Kasevich et al. ................ 128/804 |
| 4,813,429 | 3/1989 | Ethel et al. ................ 128/736 |
| 4,823,812 | 4/1989 | Eshel et al. ................ 128/804 |
| 4,967,765 | 11/1990 | Turner et al. . |
| 5,007,437 | 4/1991 | Sterzer ....................... 128/786 |
| 5,234,004 | 8/1993 | Hascoet et al. ................ 607/116 |

FOREIGN PATENT DOCUMENTS

| | | |
|---|---|---|
| 0105677 | 4/1984 | European Pat. Off. . |
| 105677 | 4/1984 | European Pat. Off. . |
| 0139607 | 5/1985 | European Pat. Off. . |
| 248758 | 12/1987 | European Pat. Off. . |
| 370890 | 5/1990 | European Pat. Off. . |
| 2639238 | 2/1991 | France . |
| 2407559 | 4/1981 | Germany . |
| 3525702 | 1/1987 | Germany . |
| 3534124 | 2/1987 | Germany . |
| 3534124A1 | 4/1987 | Germany . |
| 62-33906 | 2/1982 | Japan . |
| 62-51633 | 2/1982 | Japan . |

(List continued on next page.)

OTHER PUBLICATIONS

Pschyrembel Klinisches Wörterbuch, Walter de Gryter, Berlin, N.Y., 1986, S. 1368.

(List continued on next page.)

Primary Examiner—Lee S. Cohen
Attorney, Agent, or Firm—Cohen, Pontani, Lieberman, Pavane

[57] ABSTRACT

An apparatus for the surgical treatment of tissues by thermal effect, in particular prostate, is disclosed comprising a urethral emitting probe having a front end and a rear end, capable of being inserted in the urethra, provided with microwave antenna located intermediate or in the vicinity of said front end, said microwave antenna being connected to an external microwave generating device, and working at a frequency and at a power effective to heat said tissues to a predetermined temperature for a period of time sufficient to treat said tissues by thermal effect.

29 Claims, 4 Drawing Sheets

5,480,417
Page 2

FOREIGN PATENT DOCUMENTS

| | | |
|---|---|---|
| 63-109152 | 7/1988 | Japan. |
| 8103616 | 12/1981 | WIPO. |
| 8902292 | 3/1989 | WIPO. |
| 8905609 | 6/1989 | WIPO. |
| 92/07622 | 5/1992 | WIPO. |

OTHER PUBLICATIONS

Proceedings of the 5th International Symposium on Hyperhermic Oncology—vol. 1 of Summary Papers, "Two–element radiating endocavitary hyperthermia" by G. Biffi Gentili, A Borrani and M. Leoncini, presented at the conference "Hyperthermic Oncology 1988" in Kyoto, Japan, Aug. 29–93/88.

Poster from 5th International Symposium on Hyperthermic Oncology, Kyoto, Japan Aug. 29–Sep. 3, 1988 with reproduction of drawing used for poster.

Drawings picked up from A. Borrani's summary paper at the 5th International Symposium on Hyperthermic Oncology Kyoto, Japan Aug. 29–Sep. 3, 1988.

Abstracts of the 5th International Symposium on Hyperthermic Oncology Kyoto, Japan Aug. 29–Sep. 3, 1988.

"Local Hyperthermia of the Prostate Gland for the Treatment of Benign Prostatic Hypertrophy and Urinary Retention", A. Lindner, et al., 60 British Jouranl of Urology 567–571 (1987).

"Localized Deep Microwave Hyperthermia in the Treatment of Poor Operative Risk Patients with Benign Prostatic Hyperplasia", A. Yerushalmi, et al., The Journal of Urology 873–876 (1985).

"Further Observations on the Use of Local Hyperthermia for the Treatment of Disease of the Prostate in Man", C. Servadio, et al., 12 Eur. Urol. 101–103 (1986).

Extract from Traité d'Anatomie Humaine, 9th Ed., vol. 5, pp. 246–249 (1949), together with an English translation.

Microwave Applicator for Transurethral Hyperthermia of Benign Prostatic Hyperplasia, Astrahan et al., Int. J. Hyperthermia, 1989, vol. 5, No. 2, 283–296.

Temperaturfeldberechnungenzur Hypertermiebehandlung: Forschungsproject No. 01VF020 . AK/NT/MT298, Dorner System GmbH, Friedrichshafen, 1982, pp. 25–30.

Endotract Antenna For Application of Hyperthermia to Malignant Lesions, K. Sugimachi et al., Gann, 74, 1983, pp. 622–624.

Radiofrequency–Induced Hyperthermia in the Prostate, J. Scheblicht et al., Journal of Microwave Power, vol. 17(3), 1982, pp. 208–209.

RF Wave Heating by Trial Applicator for Gynecology, Toshimi Hasegawa et al., Proc. 3rd Annual Meeting of the Japanese Society of Hyperthermic Oncology, Nov. 13–15, 1986, Osaka, Japan.

Microwave–Induced Hyperthermia in Cancer Treatment: Apparatus and Preliminary Results, J. Mendecki et al., Int. J. Radiation Oncology, vol. 4, 1978, pp. 1095–1103.

Local Hyperthermia of the Prostate Gland for the Treatment of Benign Prostatic Hypertrophy and Urinal Retention, A Preliminary Report, A. Lindner et al., British Journal of Urology (1987), 60, pp. 567–571.

Disease of Prostate Treated by Local Microwave Hyperthermia, C. Sevadio et al., Urology, Aug. 1987, vol. XXX, No. 2, pp. 97–99.

Interstitial and Intracavitary Microwave Hyperthermia, B. Stuart Trembly, Hyperthermic Oncology 1988, vol. 2, Proceedings of the 5th International Symposium on Hyperthermic Oncology, Kyoto, Japan, 29th Aug.—3rd Sep. 1988.

Histopathological Observations in the Canine Prostate Treated by Local Microwave Hyperthermia, Z. Lieb et al., The Prostate 8:93–102 (1986).

Hyperthermiochemoradiotherapy and Esophageal Carcinoma K. Sugimachi et al., Seminars in Surgical Oncology 2:38–44 (1986).

Design and Thermometry of an Intracavitary Microwave Applicator Suitable for Treatment of Some Vaginal and Rectal Cancers, Ding–Jiu Li et al., Int. J. Radiation Oncology Biol. Phys., vol. 10, pp. 2155–2162 (1984).

Microwave Applicators For Localized Hyperthermia Treatment of Cancer of the Prostate, Mendecki et al., Journal of Radiation Oncology, vol. 6, No. 11, pp. 1583–1588, Nov., 1980.

Grand Larousse Universal, p. 8518 (1991), provided with translation.

Anatomie des Menshen, Schiebler et al. (1983).

Proceedings of the IEEE, vol. 72, No. 2, Feb. 1984, New York, pp. 224–225.

Proceedings of the 13th Northeast Bioengineering Conference, Mar. 12–13, 1987, vol. 2, *Sar Evaluation, Etc.*, pp. 390–393.

Harada et al., *Microwave Surgical Treatment of Diseases of Prostate*, Urology, Dec. 1985, vol. XXVI, No. 6, pp. 572–576.

*Transurethral Hyperthermia for BPH: Trial's Goal is to Top 80%* Success, Medical Tribune, Mar. 31, 1988, vol. 19, No. 9.

Carter, S. St. C, F.R.C.S., *Single–Session Transurethral Microwave Thermotherapy for the Treatment of Benign Prostatic Obstruction*, Journal of Endourology, vol. 5, No. 2, 1991.

Devonec, Marian, M. D., *Transurethral Microwave Heating of the Prostate–Or from Hyperthermia to Thermotherapy*, Journal of Endourology, vol. 5, No. 2, 1991.

Blute, Michael L., M. D., *Transurethral Microwave Thermotherapy for Benign Prostatic Hypertrophy*, Mediguide® to Urology, vol. 4, Issue 6.

Carter, S. et al., Prostatron Clinical Program, *Objective Clinical Results of Transurethral Microwave Thermotherapy for Benign Prostatic Obstruction*, 8th World Congress on Endourology and ESWL, Washington, D.C., Aug. 31–Sep. 2, 1990–Nov. 1990.

8th European Microwave Conference, *Multimode Square Waveguide, Etc.*, Stuchly and Stuchly, Sep. 1978, pp. 553–557.

Strohmaier, W. L., *Local Microwave Hyperthermia of Benign Prostatic Hyperplasha*, The Journal of Urology, Oct. 1990, vol. 144.

Devonec, Marian M. D., *Transurethral Microwave Thermotherapy (TUMT) in Patents with Benign Prostatic Hypertrophy*, American Urological Association—May 1990 New Orleans, La., Oct. 1990.

Carter, S. et al., Prostatron Clinical Program, *The Physics of Transuretral Microwave Thermotherapy (TUMT)*, 8th World Congress on Endourology and ESWL, Washington, D.C., Aug. 31–Sep. 2, 1990, Nov. 1990.

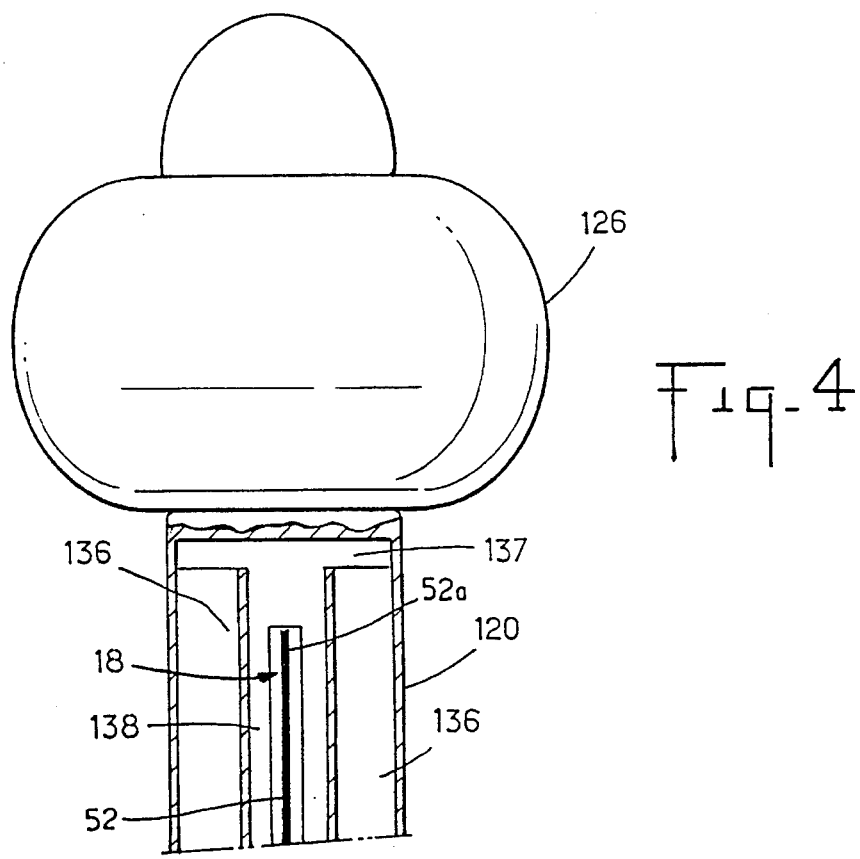
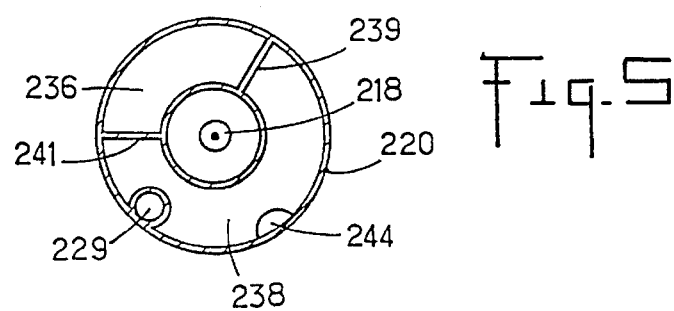
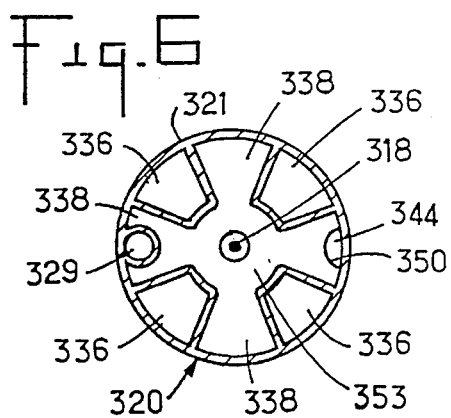
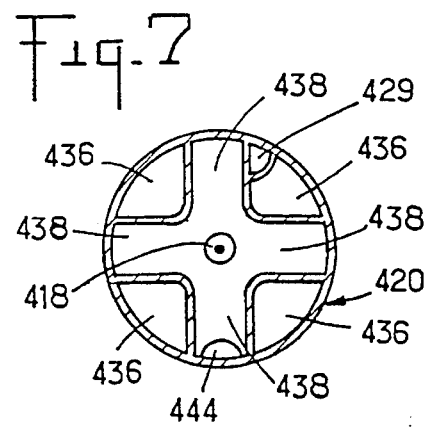

METHOD AND APPARATUS FOR THE SURGICAL TREATMENT OF TISSUES BY THERMAL EFFECT, AND IN PARTICULAR THE PROSTATE, USING A URETHRAL MICROWAVE-EMITTING PROBE MEANS This is a division, of application Ser. No. 07/667,847, filed Mar. 12, 1991, now U.S. Pat. No. 5,234,004, in turn, is a Continuation-in-part of application Ser. No. 07/438,741 filed Nov. 17, 1989, now abandoned.

FIELD OF THE INVENTION

The present invention relates to a method and apparatus for the surgical treatment of tissues by thermal effect, and in particular, the prostate, using a urethral microwave-emitting probe means.

BACKGROUND OF THE INVENTION

European patent 0,248,758 describes a microwave applicator which is inserted in the rectum for treating the prostate by hyperthermia. The microwave applicator is kept in position inside the rectum by a laterally projecting balloon, meaning that special protection of the rectum is required. Preferably, for heating the prostate, means are provided for reflecting the emitted microwaves which are then concentrated at the side of the body opening opposite to the balloon. Ducts are provided in the microwave emitting rectal applicator for circulating a cooling liquid (see page 5, lines 1 to 5).

The cooling liquid protects the rectal walls in contact with the microwave antenna from damage. Moreover, the presence of the reflecting means is absolutely necessary to prevent the antenna from emitting in all directions, when the radiation is only required to be directed onto the prostate tissues.

European patent 0,246,176 describes a catheter having an antenna equipped with a temperature sensor which is inserted into the urethra through to the bladder, for controlling the temperature reached in the urethra through use of the microwave applicator described in the above-cited European patent 0,248,758.

From a practical point of view, the design of the microwave applicator described in European patent 0,248,758 for introduction in the rectum, is not satisfactory in that the application lacks accuracy since the prostate is remotely-irradiated.

It is furthermore essential with this method to prevent the emission of microwaves in all directions, this implying an emitting antenna of very special design equipped with reflecting means for directing the radiated microwaves in only one direction, namely towards the prostate.

Also, and unquestionably, with such a device, it is quite difficult, if not impossible, to protect the sphincter, and more generally to protect the surrounding tissues. This being especially so in the case of bladder treatment.

Finally, no working frequency is disclosed.

European patent 0,105,677 describes such a microwave antenna device for hyperthermia therapy designed to be introduced in the tract or the lumen, in which device the antenna assembly is placed inside a thin supple polymer film, without any means of protecting the sensitive tissues from the heat. The working frequency is broadly disclosed as ranging between 300 and 3,000 MHz, for instance 915 MHz (page 4, lines 7 and 24).

Patent document WO-A-81/03616 to Bicher describes yet again a microwave antenna system for hyperthermia therapy, which is inserted into a body cavity and used for the treatment of cancer and similar. Typical examples of inserting apertures are the mouth and upper throat.

The introductory part of said patent document cites the document J. Microwave Power 14(2): 167–171 (1979) relative to an applicator working at a frequency of 400 or 915 MHz, introduced through the rectum for irradiation of the prostate. It is specified that said irradiation treatment involves a burning of the tissues which are close to the electrode.

According to said document, the characteristic of this irradiation treatment is that it is carried out at a lower frequency and at a higher wavelength to improve penetration into the tissues to depths of 5 to 6 cm. Such deep penetration permits extensive irradiation of large tumors in the bowels or similar.

The revue "Proceedings of the 13th Annual Northeast Bioengineering Conference, Philadelphia, Mar. 12–13, 1987, pages 390–393, Ryan" describes the pretreating by microwave-induced hyperthermia of patients suffering from biliary obstruction due to cancer, by inserting a catheter into the choledoch to allow drainage in an invasive way. The catheter works at 915 MHz.

Tests have been carried out with the same antenna in various media, as reported in FIG. 5. In the case of tests B and D, the medium was a saline solution, and it is underlined in the "Discussion" part that when the medium is changed from air to a conductive medium such as a saline or bile medium, the performances decrease dramatically, which rather discourages the specialist from using a saline solution in microwave-induced hyperthermia.

Also, it is known from Proceedings of the IEEE, 72 (1984), February, No. 2, 224–225, the advantage of using focused microwave hyperthermia applicators. It is also disclosed obtention of an optimal frequency for a fixed aperture size and a given penetration depth. FIG. 2 discloses optimal frequencies for given penetration depth of 2, 4 and 6 cm at 3,000; 1,500 and 915 MHz.

SUMMARY OF THE INVENTION

It is now a main object of the present invention to solve the new technical problem consisting in providing a solution permitting a more accurate surgical treatment of tissues by thermal effect, in particular of the prostate.

It is a further main object of the present invention to solve the above new technical problem, particularly in the thermal effect treatment of the prostate, without the need to use special probe means emitting in only one direction.

It is a further main object of the present invention to solve the new technical problem, consisting in providing a solution permitting to precisely generate the microwaves in a relatively narrow penetration field, thereby avoiding to damage the tissues surrounding the tissues to be treated by thermal effect, these surrounding tissues necessitating not to be reached by the microwaves used to perform the thermal effect treatment.

It is another main object of the present invention to solve the new technical problem consisting in providing a solution permitting to perform the treatment of tissues by thermal effect in a localized manner, while providing a possibility of adapting the thermal effect treatment to the shape and the size of the tissues to be treated.

It is another object of the present invention to solve the aforesaid new technical problems in a semi-invasive way, namely by using the natural body cavities or body lumens.

All these technical problems are solved for the first time by the present invention, extremely simply, inexpensively, with greater accuracy and reliability in a manner exploitable on an industrial scale.

According to a first aspect, the present invention provides a method for the surgical treatment of tissues by thermal effect, in particular prostate, comprising using an emitting probe having a front end and a rear end, capable of being inserted in a bodylumen, said emitting probe comprising a microwave antenna means located intermediate or in the vicinity of said front end, said microwave antenna means being connected to an external microwave generating device and generating microwaves through said microwave antenna means towards said tissues to be treated with said microwave generating device, at a frequency of about 1300 MHz±50 MHz and a power effective to heat said tissues to a predetermined temperature for a period of time sufficient to treat said tissues by thermal effect.

According to the present invention, the thermal effect is preferably a "thermotherapy", that means that the tissues are treated by heat energy at a temperature higher than 45° C. and preferably ranging between about 45° C. and not more than about 85° C., during a period of time sufficient to reach necrosis of the tissues submitted to the thermal effect.

Thermal effect treatment according to the preferred invention embodiment is fully different from the hyperthermia treatment of the prior art since hyperthermia is limited to a temperature range lower than 45° C. and generally of 40° C.–43° C. The invention is based on the discovery of unexpected positive therapeutical effects provided by a heating of tissues at a temperature higher than 45° C. versus a heating of said tissues at a temperature lower than 45° C. But, the invention can also be used to perform a hyperthermia treatment.

According to a preferred embodiment, said emitting probe is a urethral probe capable of being inserted in the urethra, and comprises positioning means to position and maintain the positioning of the urethral probe in the urethra. Preferably, the positioning means comprise an inflatable urethral balloon means located between said microwave antenna means and said front end, said method further comprising inserting said urethral emitting probe with said balloon means not inflated into the urethra up to the level of the tissues to be treated by thermal effect, at which level said urethral balloon means reaches the bladder, inflating said urethral balloon means to lock the front end of the urethral probe in the bladder neck.

According to a particular embodiment, the invention provides a method for the surgical treatment of tissues by thermal effect, in particular prostate, comprising using a urethral emitting probe having a front end and a rear end, capable of being inserted in the urethra, said urethral emitting probe comprising a microwave antenna means located intermediate or in the vicinity of said front end, said microwave antenna means being connected to an external microwave generating device, said urethral probe means comprising cooling means fed with a cooling medium, said cooling means extending up to the full length of the microwave antenna means, generating microwaves through said microwave antenna means towards said tissues to be treated with said microwave generating device, at a frequency and a power effective to heat said tissues to a predetermined temperature for a period of time sufficient to treat said tissues by thermal effect, and feeding a cooling medium to said cooling means during generation of said microwaves, to prevent burns on the walls of the urethra in contact with the probe means.

Preferably, microwaves are generated at a frequency of about 1300 MHz±50 MHz.

According to a specific feature, the emitting probe is a urethral probe and comprises positioning means to position and maintain the positioning of the urethral probe in the urethra.

According to another specific feature, the positioning means comprise an inflatable balloon means located between said microwave antenna means and said front end, said method comprising inserting said urethral emitting probe with said balloon means not inflated into the urethra up to the level of the tissues to be treated by thermal effect, at which level said balloon means reaches the bladder, inflating said balloon means to lock the front end of the urethral probe in the bladder neck.

According to a further embodiment, the invention provides a method for the surgical treatment of tissues by thermal effect, in particular prostate, comprising:

providing
  a) an urethral emitting probe having a front end and a rear end, capable of being inserted in the urethra, said urethral emitting probe comprising a microwave antenna means located intermediate or in the vicinity of said front end, said microwave antenna means being connected to an external microwave generating device;
  b) a rectal probe means comprising control means for controlling the positioning of the urethral probe means; and
  c) a central control device receiving the information provided by the control means for controlling the positioning of the urethral probe means,
inserting said urethral emitting probe into the urethra up to the level of the tissues to be treated by thermal effect,
controlling the positioning of the urethral probe means with said control device from information received by said control means, optionally correcting the positioning of the urethral probe means; and
generating microwaves through said microwave antenna means towards said tissues to be treated with said microwave generating device, at a frequency and a power effective to heat said tissues to a predetermined temperature for a period of time sufficient to treat said tissues by thermal effect.

According to a further embodiment, the invention provides a method for the surgical treatment of tissues by thermal effect, in particular prostate, comprising:
  a) providing a urethral emitting probe having a front end and a rear end, capable of being inserted in the urethra, said urethral emitting probe comprising a microwave antenna means located intermediate or in the vicinity of said front end, said microwave antenna means being connected to an external microwave generating device, and an inflatable balloon means located between said microwave antenna means and said front end,
  a rectal probe means comprising an echographic probe connected to a screen equipped echograph and to a central control device for receiving the information provided by said echographic probe and controlling the positioning of the urethral probe means,
  b) inserting said urethral emitting probe with said balloon means not inflated into the urethra up to the level of the tissues to be treated by thermal effect, at which level said balloon reaches the bladder, inflating said balloon means to lock the front end of the urethral probe in the bladder neck, c) controlling the positioning of the urethral probe means with the information transmitted to said central control device from said echographic probe, optionally correcting the positioning of the urethral probe means by way of deflating and inflating again said balloon means, d) generating microwaves through said microwave antenna means towards said tissues to be treated with said microwave generating device, at a frequency and a power effective to heat said tissues to a predetermined temperature for a period of time sufficient to treat said tissues by thermal effect.

According to another further embodiment, the invention provides a method for the surgical treatment of tissues by thermal effect, in particular prostate, comprising:

a) providing a urethral emitting probe having a front end and a rear end, capable of being inserted in the urethra, said urethral emitting probe comprising a microwave antenna means located intermediate or in the vicinity of said front end, said microwave antenna means being connected to an external microwave generating device, comprising power adjusting means for adjusting the power of the microwaves, an inflatable balloon means located between said microwave antenna means and said front end, and at least one urethral temperature sensor located in the vicinity of the microwave antenna means for detecting urethral temperature, a rectal probe means comprising control means for controlling the positioning of the urethral probe means, and a central control device receiving the information provided by the control means for controlling the positioning of the urethral probe means, said rectal probe comprising at least one rectal temperature sensor for detecting the rectal temperature at the level of the rectal wall facing the tissues to be treated, and transmission means to transmit said temperature data recorded by said urethral and rectal temperature sensors to a thermometry device and to said central control device, b) inserting said urethral emitting probe with said balloon means not inflated into the urethra up to the level of the tissues to be treated by thermal effect, at which level said balloon reaches the bladder, inflating said balloon means to lock the front end of the urethral probe in the bladder neck, c) generating microwaves through said microwave antenna means towards said tissues to be treated with said microwave generating device, at a frequency and a power effective to heat said tissues to a predetermined temperature for a period of time sufficient to treat said tissues by thermal effect, d) detecting the respective urethral and rectal temperatures provided by the urethral and rectal temperature sensors, during said microwaves generating step c), and e) adjusting at least the power of the microwaves, when the temperature detected selected from the urethral temperature and the rectal temperature is not conform to said predetermined temperature range.

According to still another invention embodiment, the invention provides a method for the surgical treatment of tissues by thermal effect, in particular prostate, comprising:

a) providing a urethral emitting probe having a front end and a rear end, capable of being inserted in the urethra, said urethral emitting probe comprising a microwave antenna means located intermediate or in the vicinity of said front end, said microwave antenna means being connected to an external microwave generating device, comprising power adjusting means for adjusting the power of the microwaves, an inflatable balloon means located between said microwave antenna means and said front end, and at least one urethral temperature sensor located in the vicinity of the microwave antenna means for detecting urethral temperature, said urethral probe means comprising cooling means fed with a cooling medium, said cooling means extending up to the full length of the microwave antenna means, a rectal probe means comprising control means for controlling the positioning of the urethral probe means, and a central control device receiving the information provided by the control means for controlling the positioning of the urethral probe means, said rectal probe comprising at least one rectal temperature sensor for detecting the rectal temperature at the level of the rectal wall facing the tissues to be treated, and transmission means to transmit said temperature data recorded by said urethral and rectal temperature sensors to a thermometry device and to said central control device, b) inserting said urethral emitting probe with said balloon means not inflated into the urethra up to the level of the tissues to be treated by thermal effect, at which level said balloon reaches the bladder, inflating said balloon means to lock the front end of the urethral probe in the bladder neck, c) generating microwaves through said microwave antenna means towards said tissues to be treated with said microwave generating device, at a frequency and a power effective to heat said tissues to a predetermined temperature range for a period of time sufficient to treat said tissues by thermal effect, d) detecting the respective urethral and rectal temperatures provided by the urethral and rectal temperature sensors, during said microwaves generating step c), and e) adjusting one or both of the power of the microwaves and of the cooling temperature of the cooling means, when the temperature detected selected from the urethral temperature and the rectal temperature is not conform to said predetermined temperature range.

According to a specific embodiment, the process comprises providing the rectal probe with an inflatable balloon element mounted around the rectal probe on its front end and with inflating means comprising a liquid medium, preferably a radio reflecting liquid medium, said method comprising inflating said inflatable balloon element when said rectal probe is inserted in the rectum and feeding liquid medium, preferably a radio reflecting liquid medium through said rectal probe feeding means, thereby providing heat protection of the rectal walls.

According to another specific embodiment, the process comprises providing the external microwave generating device with microwaves generating means capable of emitting microwaves at a working frequency of about 900 MHz and at a power which is adjustable up to 100 Watts.

According to a second aspect, the present invention provides a patentably distinct embodiment comprising providing microwaves generating means capable of emitting at a working frequency of about 1,300 MHz±50 MHz.

According to a specific feature, means are provided for selecting the working frequency of the microwaves in function of the size of the tissues to be treated by thermal effect.

According to a third aspect, the present invention provides an apparatus for the surgical treatment of tissues by thermal effect, in particular prostate, comprising an emitting probe having a front end and a rear end, capable of being inserted in a body lumen, said emitting probe comprising a microwave antenna means located intermediate or in the vicinity of said front end, said microwave antenna means being connected to an external microwave generating device, and said external microwave generating device comprising microwaves generating means adapted for generating microwaves at a frequency of about 1300 MHz±50 MHz and a power effective to heat said tissues to a predetermined temperature for a period of time sufficient to treat said tissues by thermal effect.

According to a preferred embodiment, the emitting probe is a urethral probe capable of being inserted in the urethra, positioning means are provided to position and maintain in position the urethral probe in the urethra. Preferably, said positioning means comprise an inflatable urethral balloon means located between said microwave antenna means and said front end, and urethral inflating means for inflating said urethral balloon means, said balloon reaching the bladder when said urethral probe is positioned in the urethra.

Advantageously, the urethral inflating means comprise a liquid medium.

According to a specific embodiment, the present invention provides an apparatus, wherein said urethral inflating means for inflating said urethral balloon means comprise an electroconductive liquid forming a radio reflecting screen capable of reflecting the microwaves emitted by said microwave antenna means, thereby protecting the bladder from being damaged by said microwaves.

According to another specific embodiment, the present invention provides an apparatus for the surgical treatment of tissues by thermal effect, in particular prostate, comprising a urethral emitting probe having a front end and a rear end, capable of being inserted in the urethra, said urethral emitting probe comprising a microwave antenna means located intermediate or in the vicinity of said front end, said microwave antenna means being connected to an external microwave generating device, said urethral probe means comprising cooling means fed with a cooling medium, said cooling means extending up to the full length of the microwave antenna means, said microwave generating device being adapted for generating microwaves at a frequency and at a power effective to heat said tissues to a predetermined temperature for a period of time sufficient to treat said tissues by thermal effect, and preventing burns on the walls of the urethra in contact with the urethral probe means due to said cooling medium.

The frequency is preferably about 1300 MHz±50 MHz. Advantageously, the apparatus comprises positioning means to position and maintain the urethral probe in the urethra. Said positioning means can comprise an inflatable balloon means located around the front end of the urethral probe to reach the bladder when said urethral probe is in the urethra.

According to a further embodiment, the present invention provides an apparatus, wherein said inflatable balloon means is inflated with a liquid medium, in particular an electrically conductive liquid forming radio reflecting means, thereby protecting the bladder from a heating by said microwaves.

According to another embodiment, the present invention provides an apparatus for the surgical treatment of tissues by thermal effect, in particular prostate, comprising:

a) a urethral emitting probe having a front end and a rear end, capable of being inserted in the urethra, said urethral emitting probe comprising a microwave antenna means located intermediate or in the vicinity of said front end, said microwave antenna means being connected to an external microwave generating device;

b) a rectal probe means comprising control means for controlling the positioning of the urethral probe means; and c) a central control device receiving the information provided by the control means for controlling the positioning of the urethral probe means, d) correcting means for correcting the positioning of the urethral probe means, and e) said external microwave generating device comprising microwaves generating means adapted for generating microwaves at a frequency and at a power effective to heat said tissues to a predetermined temperature for a period of time sufficient to treat said tissues by thermal effect.

According to another embodiment, the present invention provides an apparatus for the surgical treatment of tissues by thermal effect, in particular prostate, comprising:

a) providing a urethral emitting probe having a front end and a rear end, capable of being inserted in the urethra, said urethral emitting probe comprising a microwave antenna means located intermediate or in the vicinity of said front end, said microwave antenna means being connected to an external microwave generating device, and an urethral inflatable balloon means located between said microwave antenna means and said front end to reach the bladder, when said urethral probe is in the urethra;

urethral inflating means for inflating said urethral balloon means to lock the front end of the urethral probe in the bladder neck, a rectal probe comprising an echographic probe connected to a screen equipped echograph and to a central control device for receiving the information provided by said echographic probe and controlling the positioning of the urethral probe means, correcting means for correcting the positioning of the urethral probe means, said external microwave generating device comprising microwaves generating means adapted for generating microwaves at a frequency and at a power effective to heat said tissues to a predetermined temperature for a period of time sufficient to treat said tissues by thermal effect, thereby having an echographic control of the surgical treatment of said tissues.

According to another embodiment, the present invention provides an apparatus for the surgical treatment of tissues by thermal effect, in particular prostate, comprising:

a urethral emitting probe having a front end and a rear end, capable of being inserted in the urethra, said urethral emitting probe comprising a microwave antenna means located intermediate or in the vicinity of said front end, said microwave antenna means being connected to an external microwave generating device, an urethral inflatable balloon means located between said microwave antenna means and said front end, and at least one urethral temperature sensor located in the vicinity of the microwave antenna means for detecting urethral temperature, a rectal probe means comprising control means for controlling the positioning of the urethral probe means, and a central control device receiving the information provided by the means for controlling the positioning of the urethral probe means, said rectal probe comprising at least one rectal temperature sensor for detecting the rectal temperature at the level of the rectal wall facing the tissues to be treated, and transmission means to transmit said temperature data recorded by said urethral and rectal temperature sensors to a thermometry device and to said central control device, said external microwave generating device comprising microwaves generating means adapted for generating microwaves at a frequency and at a power effective to heat said tissues to a predetermined temperature range for a period of time sufficient to treat said tissues by thermal effect, said central control device comprising power and cooling temperature adjusting means to adjust one or both of the microwaves power and of the cooling temperature of the cooling means, when the temperature detected selected from the urethral temperature and from the rectal temperature is not conform to said predetermined temperature range.

According to another embodiment, the invention provides an apparatus comprising providing the rectal probe with a rectal inflatable balloon element mounted around the rectal probe on its front end and with rectal inflating means comprising an inflating liquid medium and feeding means for feeding said liquid medium through said rectal probe inflating means, thereby providing heat protection of the rectal walls. This inflating liquid can be advantageously a radioreflecting liquid in particular by being electroconductive.

According to a further embodiment, the invention provides an apparatus comprising providing the rectal probe with radio reflecting means to protect the rectal walls from heat.

According another embodiment, the present invention provides an apparatus, wherein said urethral temperature sensor comprises a plurality of strands of optical fibers placed in radially and/or longitudinally offset fashion in the longitudinal direction of the urethral emitting probe.

According to a further embodiment, the present invention provides an apparatus, wherein said urethral probe means comprises cooling means fed with a cooling medium, said cooling means extending up to the full length of the microwave antenna means, said cooling means comprising cooling ducts arranged symmetrically with respect to a symmetry plane of said urethral emitting probe, said urethral temperature sensors and said balloon inflating means being located opposite in the same symmetry plane passing through the axis of the urethral probe means.

According to a particularly preferred embodiment, the present invention provides an apparatus, wherein the external microwave generating device is adapted for emitting microwaves at a frequency of about 1300 MHz±50 MHz and at a power which is adjustable up to 100 watts.

According to another less preferred embodiment, the present invention provides an apparatus, wherein said external microwave generating device is capable of generating microwaves at a frequency of about 900 MHz and at a power adjustable up to 100 watts.

According to the present invention, it is possible to treat benign or malignant tissues by coagulation of cytoplasmic proteins or by a myorelaxing effect on the muscular fibers, or a bacteriostatic effect, or to treat localized cancers of the bladder or prostate, or prostatitis or cystitis, and more generally to perform the treatment of benign prostatic hypertrophy.

Further, the ability to cool the urethra allows for more effective heat delivery to the centre of the prostatic lateral lobes with preservation of the periurethral tissues.

This ensures an increase therapeutic tissue destruction within the prostate leading to a more effective improvement in voiding status that has been found with the prior art prostatic microwave hyperthermia devices.

Furthermore, according to the invention, process and apparatus, the overall operations are accomplished in most patients with a single session, anesthesia free treatment.

Further, with the help of a balloon self-retaining device provided at the front end of the urethral probe, it is rendered possible a quick and precise positioning of the microwave antenna means within the prostatic urethra in relation to the bladder neck.

Furthermore, with the help of the cooling means for cooling the urethral probe, it is possible to lower the temperature of the urethra walls during treatment with accuracy by controlling the flow of the cooling medium and/or the temperature of the cooling medium.

Further, the monitoring of the temperature of the urethra wall is safely and accurately effected with the presence of temperature sensors combined with the uretral probe. Additionally by incorporating also temperature sensors with the rectal probe, it is possible to monitor the temperature at the rectal wall. By providing a central control module, notably comprising a technical computer, it is possible for the physician to control precisely the power output of the unit in response to the temperature measured by the urethral and/or rectal thermosensors. The achieved urethral and/or rectal temperatures and power output are displayed in real time and recorded by the computer for subsequent analysis. Print out of the treatment parameters and temperature tracings are preferably available for inclusion in each individual patient record.

It is also preferred to have safety devices incorporated in the invention apparatus, to prevent the excessive delivery of energy. These safety devices preferably include a thermometry feed-back system which maintains the temperature at not more than 44.5° C. at the level of the urethral walls as measured by the urethral regulating thermosensors, and at not more than 42.5° C., at the level of the rectal walls as measured by the rectal thermosensors.

It is preferred that the thermometry system is of the fiber optical type designed to accurately measure the temperature within the microwave field.

According to a specific feature, the rectal probe is provided with several optical thermosensors, in particular at least three optical thermosensors disposed in radially and/or longitudinally offset fashion in the longitudinal direction of the probe means, in such a way as to detect the temperature in various radial and/or longitudinal directions of the probe means.

According to an advantageous variant of embodiment, said apparatus comprises heat protecting means for protecting from the heat the sensitive tissues other than the tissues to be treated, said means preferably comprising means forming radioreflecting screen. Said apparatus may also be characterized in that one of the means forming radioreflecting screen is placed at the level of an organ to be protected, such as the bladder, the sphincter.

Preferably, another part of the means forming radioreflecting screen protects the rectal wall from high temperatures.

A fourth aspect of the invention is also to provide an apparatus for the surgical treatment of tissues by thermal effect, and in particular the prostate, which apparatus comprises heating means for producing microwaves, said heating means being situated in an emitting probe means adapted to be inserted in a body cavity, wherein said apparatus comprises heat protecting means for protecting from the heat the sensitive tissues other than the tissues to be treated, preferably comprising means forming radioreflecting screen.

According to a particlarly advantageous embodiment of the invention, the means which, according to the invention, form radioreflecting screen, contain a radioreflecting liquid medum. Advantageously, said radioreflecting liquid medium is an electrically conductive liquid reflecting the microwaves.

According to a variant embodiment, the radioreflecting screen-forming means according to the invention comprise at least one wire, parallel to the mean electrical field.

According to a currently preferred application to the treatment of the prostate, the apparatus according to the invention is characterized in that the probe means is a urethral probe means inserted in the urethra up to the level of the prostate. Preferably, one part of the means forming radioreflecting screen according to the invention is at the level of an organ to be treated, such as the bladder, the sphincter.

According to another particularly advantageous embodiment of the invention, said means forming radioreflecting screen and protecting the bladder may comprise a urethral balloon provided on the front end of the antenna, urethral inflating means being provided for inflating said balloon with a radioreflecting conductive solution.

According to a variant embodiment, the screen-forming means protecting the bladder comprise a conductive solution injected directly into the bladder, said solution being preferably hypertonic.

According to another particularly advantageous embodiment of the invention, another part of said screen-forming means is fast with a rectal probe means, for protecting the rectal wall from high temperatures.

Thus, according to a variant embodiment of said means forming protection screen for the rectal wall, said means can comprise a radioreflecting liquid medium, in particular one introduced into a rectal balloon provided around the front end of the rectal probe means.

Means for immobilizing the rectal probe means in position can be provided, said means preferably permitting a rotation of said probe means around its axis. Said immobilizing means preferably comprise a rectal balloon, for example in latex, which surrounds the rectal probe means, and inside which said probe means can be readily oriented from the outside.

According to one particular variant of embodiment, said microwave generating device comprises an inner conductor comprising a metallic cable coaxial to the probe means covered by an electrically insulating sleeve over its whole length, and an outer conductor extending over part of the length of the inner conductor, the emitting microwave antenna means being defined by the front part of the inner conductor, which ends at an intermediate level of the emitting probe means.

According to yet another particularly advantageous variant of embodiment, said temperature sensing means comprise a fiber-optic thermometer, heat-insulated from the cooling circuit, preferably comprising several strands of fibers disposed in radially and/or longitudinally offset fashion in the longitudinal direction of the probe means, in such a way as to detect the temperature in various radial and/or longitudinal directions of the probe means.

It is therefore obvious that the apparatus according to the invention, the emitting probe means can be positioned with great accuracy since it is inserted directly into the prostate along the natural urethral passage, thus preventing the sphincter from being damaged.

Furthermore, by setting the frequency of the microwave means at a value of about 1,300 MHz±50 MHz, it is unexpectedly obtained a very efficient thermal effect treatment of the prostate in the centre thereof, enabling in a single session to treat the full volume of the prostate by thermal effect.

Also, owing to the radioreflecting screen-forming means according to the invention, it becomes possible to protect efficiently the bladder as well as the rectal walls. It is possible, according to the invention, to use a probe means which preferably emits in one given direction.

Understandably, therefore, all the decisive technical advantages, unexpected by anyone skilled in the art, and listed hereinabove, are obtained according to the invention, and moreover, the proposed apparatus is very versatile and very easy to handle for a practitioner.

BRIEF DESCRIPTION OF THE DRAWINGS

The invention will be more readily understood on reading the following description of several embodiments of an apparatus according to the invention for the surgical treatment of tissues by thermal effect in a preferred application to the treatment of the prostate, reference being made to the accompanying drawings, in which:

FIG. 2a is a cross-section along line IIa—IIa of FIG. 2;

FIG. 4 illustrates a variant embodiment of the urethral emitting probe means according to the invention, showing a longitudinal axial section of a second embodiment of the cooling means;

FIG. 5 illustrates another variant embodiment of the structural design of the urethral emitting probe means, showing an axial cross-section of another embodiment of the cooling means;

FIG. 6 illustrates another variant of the cooling means in a view similar FIG. 5;

FIG. 7 illustrates yet another variant embodiment of the cooling means in a view similar to FIG. 5.

DETAILED DESCRIPTION OF PREFERRED EMBODIMENTS

Figure 1:
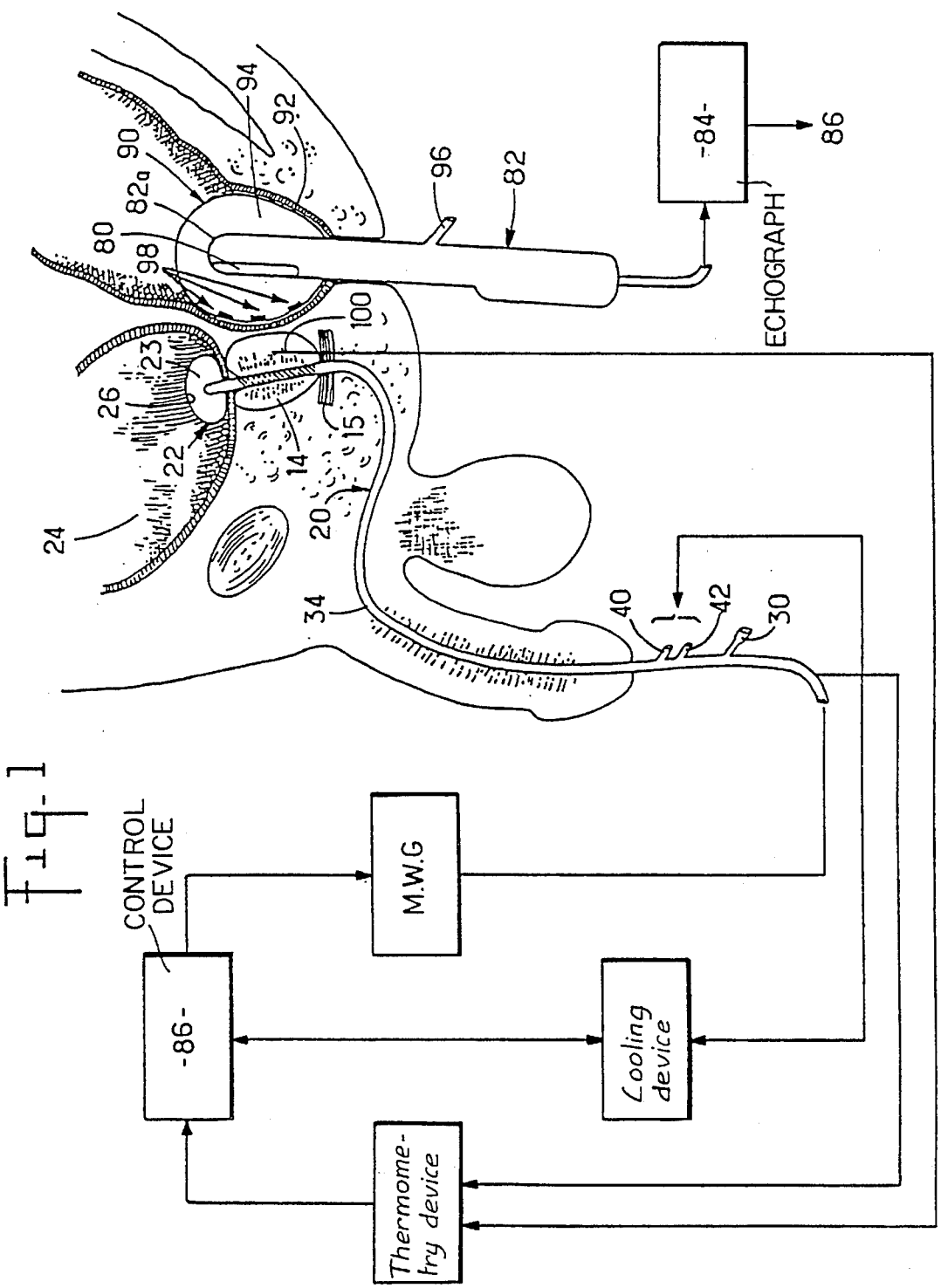
FIG. 1 a diagrammatical view of a partial section of the complete apparatus according to the invention for the surgical treatment of tissues to be destroyed by thermal effect, illustrated in its preferred application to the treatment of the prostate, and comprising a urethral emitting probe means and a rectal echographic detecting probe means, both connected to a central control device.
Figure 2:
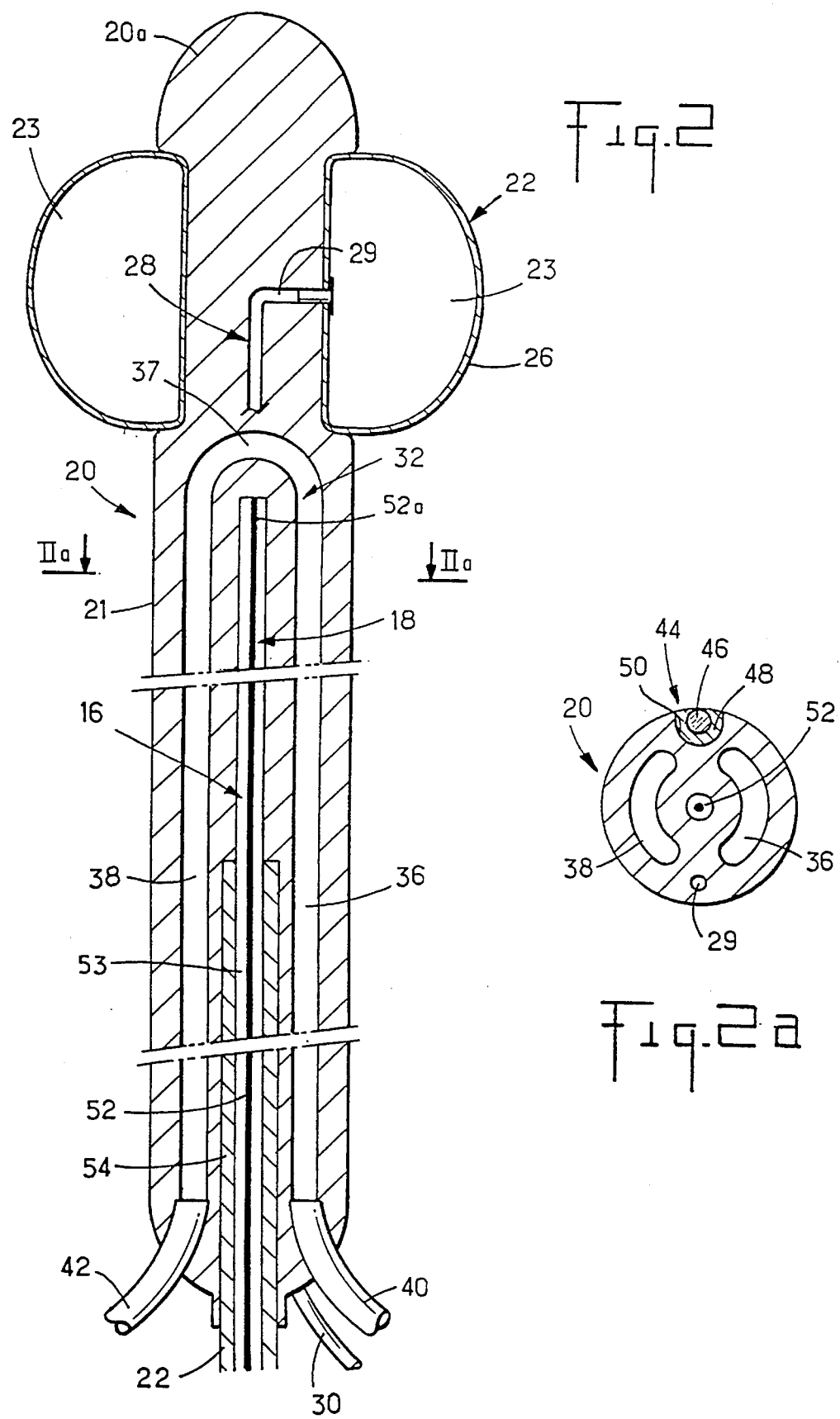
FIG. 2 is a view showing a partial longitudinal axial section of the main part of the urethral emitting probe means.

Referring in particular to FIG. 1, this shows an apparatus according to the invention, bearing the general reference number 10, for the surgical treatment of tissues 12 by thermal effect, preferably the prostate 14, of the type comprising heating means 16 for inducing thermal effect, consisting of a microwave generating device 18, clearly shown in FIG. 2, placed in a emitting probe means of general reference number 20, shown in longitudinal axial section in FIG. 2, adapted to be inserted in a cavity of the body. The microwave generating device is capable of generating microwaves at a frequency of 1,300 MHz±50 MHz. Frequency setting means are also provided to set the frequency precisely at a frequency value within the range of 1,300 MHz±50 MHz.

In a preferred embodiment, the emitting probe means 20 is designed so as to be insertable within a lumen body of an animal, in particular a human being, this probe being preferably insertable within the urethra thereby constituting a urethral probe means.

According to a preferred embodiment, means for sensing the electrical field and/or means for sensing the temperature are present, preferably within a rectal probe means 82.

According to a specific preferred embodiment, the emitting probe means 20 comprises a front end 20a provided with positioning means 26 to position and maintain in position the urethral probe in the urethra. Preferably, said positioning means comprise a balloon means which can be of the Foley type which can be inflated or deflated at will with a liquid medium and which is helpful for inserting quickly the emitting probe, when it is a urethral one, when the balloon is deflated, into the urethra up to the level of the tissues to be treated by thermal effect, at wich level said balloon means reaches the bladder, so that, after inflating said balloon means with said liquid medium, the front end of the urethral probe 20 is locked in the bladder neck, thereby reaching a precise positioning of the microwaves antenna means with regard to the prostate and maintaining this positioning during the whole treatment as clearly seeen in FIG. 1.

The apparatus according to the invention is characterized in that it comprises heat protecting means 22, 30 for protecting the sensitive tissues other than the tissues 12 to be destroyed, such as the prostate 14, said means preferably comprising means forming radioreflecting screen 22, 30.

According to a variant embodiment of the invention, the means forming radioreflecting screen comprise a radioreflecting liquid medium, preferably an electrically conductive medium able to reflect the microwaves emitted by the emitting probe means 20 equipped with the microwave emitting device 18.

According to a particular variant of embodiment, said radioreflecting conductive solution is injected directly into the patient's bladder 24. In this case, said solution is preferably hypertonic. It can be, for example, a solution with a high ion concentration, such as by using NaCl. In general, suitable conductive solutions are saturated ionic solutions, such as NaCl or nitrate solutions, said solutions are obvious to anyone skilled in the art.

According to another variant of embodiment, one part 22 of the screen forming means is placed at the level of an organ to be protected, in particular the bladder. According to a preferred embodiment, said means forming protection screen for the bladder comprises said urethral balloon 26 provided on the front end 20a of the probe means 20. Said balloon 26 is equipped with inflating means 28 for inflating it with a liquid medium preferably with a radioreflecting conductive solution 23. Said inflating means normally comprise an internal duct 29 extending out towards a flexible tube 30. Said radioreflecting conductive solution may be identical to the previous one and based on saturated NaCl solution.

According to one advantageous embodiment of the emitting probe means according to the invention, said probe means comprises cooling means 32 incorporated to the probe means 20 for lowering the temperature of the external wall of said probe means 20, namely, in the illustrated case, the walls of the urethra 34. Said cooling means 32 consists, for example, in at least two conduits, respectively an inlet conduit 36 and an outlet conduit 38, containing the cooling medium and communicating with each other at the front of the probe means 20 via a connection conduit 37 clearly shown in FIG. 2. Said conduits 36, 38 communicate with flexible tubes 40, 42, respectively a supply tube and a discharge tube for the cooling medium, which may be water.

Figure 3:
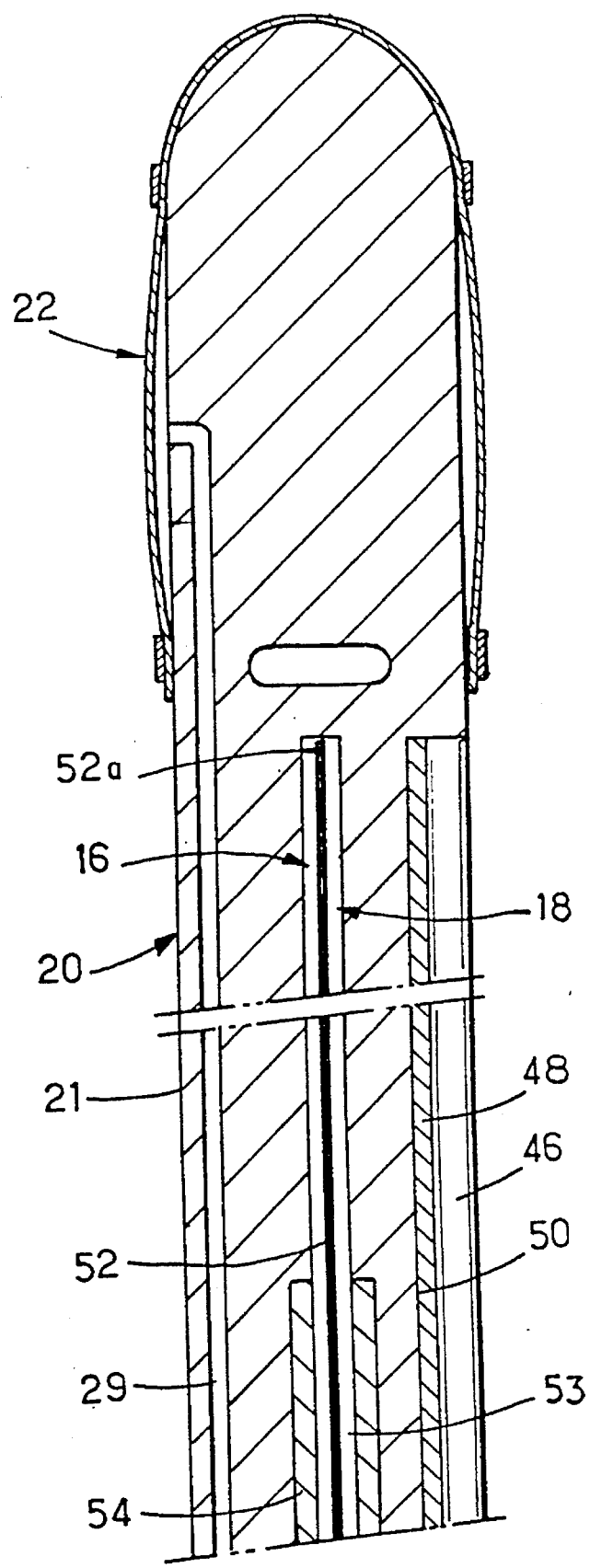
FIG. 3 is a perspective side view of the urethral emitting probe means shown in FIGS. 1 and 2, the positioning means, preferably a urethral balloon being deflated.

According to another characteristic of the invention, the urethral emitting probe means 20 is equipped with means 44 for sensing the temperature on or inside the urethral probe means 20. According to an advantageous variant, said temperature sensor 44 comprises a fiber-optic thermometer 46, the optical fibers being isolated by heat-insulating means 48 from the rest of the probe means and in particular from the cooling circuit 36, 38, as illustrated in FIGS. 2a and 3. Said thermometer comprises a plurality of strands of fibers placed in radially and/or longitudinally offset fashion in the longitudinal direction of the probe means 20, in such a way as to detect the temperature in various radial and/or Longitudinal positions of the probe means.

Said thermometer 46 and associted insulating means 48 may be disposed in a Longitudinal slot 50 provided in the external surface 21 of the probe means 20.

It will be noted that, advantageously, the front end 20a of the probe means 20 should be rounded to facilitate insertion of the probe means 20 through the urethra and up to the bladder 24, as can be seen in FIG. 1.

The microwave generating device 16, as illustrated in FIGS. 2 and 3, comprises an inner conductor 52 constituted by a metallic cable coaxial to the probe means 20 and covered with an electrically insulating sleeve 53 over its whole length, and an outer conductor 54 extending over part of the length of the inner conductor. The emitting microwave antenna means is defined by the front part 52a of the inner conductor 52 free of outer conductor 54. The inner conductor has its front part 52a located at an intermediate part of the probe to leave space for the positioning means 22, the length of the front part 52a forming antenna means is preferably about one fourth of the microwave wavelength. Preferably, the free end of the cable 52a forming microwave emitting antenna ends up under the urethral balloon 26 forming the means protecting the bladder. Said cable 52 forms an emitting antenna which may be for example 20 to 40 mm long and which radiates in all directions about its axis, i.e. over 360°.

Said emitting antenna 52a constituted by the non-insulated part of the cable 52 is connected to a microwave generator apparatus symbolized by the initials M. W. G., emitting preferably at about 1300 MHz±50 MHz, and of power adjustable up to 50 W or even 100 W, thereby reaching a most effective thermal effect treatment of the tissues to be treated.

According to a variant of embodiment, the emitting antenna may be rather more complex and comprise shielding portions along the non-insulated part of cable 52, this with a view to preferentially heating certain parts of the prostate.

FIG. 2a shows an axial cross-section of the emitting probe means 20, and illustrates the shape and position of each one of the elements constituting the probe means. This figure shows that the conduits 36, 38 containing the cooling medium, such as water, are formed by wide openings extending over an arc of circle of the probe means 20 which latter has a substantially circular or slightly ovoidal cross-section for easy passage through the urethra. It is observed that according to the variant embodiment illustrated in FIG. 2a, the temperature sensor 44 and the duct 29 supplying the balloon 26 are situated in substantially the same plane passing through the axis of the probe means, hence of the cable 52, whereas the conduits 36, 38 containing the cooling medium are also arranged symmetrically with respect to said plane of symmetry.

Other variants of structure of the urethral probe means 20 are shown in FIGS. 4 to 7 in which the same reference numbers increased by 100, are used to designate identical parts or parts having the same function.

In the embodiment shown in FIG. 4, the urethral probe means designated by the general reference 120 comprises an annular duct 136 coaxial to the probe means 120 communicating with a disc-shaped common duct 137 reaching to a central conduit 138 in which is introduced the microwave-emitting device 18.

Referring now to FIG. 5, this shows another embodiment of the internal structure of the probe means, of which the general reference number has, in this example, been increased of 200, giving it the reference 220. As shown in this figure, the inlet conduit 236 supplying the cooling medium, occupies an annular sector of the probe means 220, whereas the outlet conduit 238 discharging the heated cooling medium, occupies a complementary annular sector, both annular sectors 236, 238 being separated by longitudinal transversal partitions 239, 241. The emitting device 218 is always placed axially with respect to the probe means 220. FIG. 5 also shows the conduit 229 supplying the inflating medium, such as for example an electrically conductive liquid, to the balloon provided on the front end of the probe means 220, as well as the temperature sensor 244.

FIG. 6 illustrates another variant of embodiment in which the parts which are identical or have the same function have been given the same reference numbers, further increased by 100. According to said FIG. 6, four inlet conduits 336 supplying the cooling medium are provided, said conduits occupying annular sectors of the probe means 320 from the periphery 321 to the central longitudinal orifice 353 in which the microwave-emitting device 318 is inserted. The remaining sectors comprise corresponding annular conduits 338 for discharging the cooling medium, a conduit 329 being also provided for inflating the balloon as well as a slot 350 for housing the temperature sensor 344.

Referring to FIG. 7, this shows yet another variant of the structure of the probe means of which the reference number has been further increased by 100, making it then 420. Four cooling medium inlet sectors 436 are also provided here, said sectors having rounded edges so that the remaining sectors 438 are substantially cross-shaped, which remaining cooling medium outlet sectors may be intercommunicating or not. The emitting device 418 is also placed in the axis of the probe means 428.

It is therefore understood that various forms of embodiment are possible for the structure of the emitting probe means. The probe means structure such as described and illustrated in FIGS. 1 through 7, forms an integral part of the invention and is incorporated in the description by way of reference.

The apparatus according to the invention further comprises control means 80 for controlling the positioning of the urethral probe means 20, said control means 80 being preferably incorporated in a rectal probe means 82. Said control means 80 are preferably constituted by an echographic probe 82 of rectal type. Said echographic probe is advantageously connected with a screen-equipped echograph 84. In a variant embodiment, the echographic probe may be connected to a central control device 86 centralizing all the information and capable of- automatically controlling the microwave generator device M. W. G. as a function of the recorded temperature data and of any data which may have been programmed by the practitioner, as can be understood from FIG. 1.

The central control device 86, such as a computer or the like, receives all the temperature data centralized in a thermometry device as well as the temperature data from the cooling device supplying the cooling means of the emitting probe means 20; it also give the instructions necessary to the microwave generating device (M.W.G.) as well as to the cooling device with the purpose of either notifying the cooling flow and/or the cooling temperature. According to a variant embodiment, it can also receive the data issued from the echographic probe 82 relatively to the position of the emitting probe means 20 in relation to the prostate.

An intersticial thermometer 100 may also be provided, inserted in the prostate 14, under echographic control, so that when biopsies have to be carried out, it is possible to detect the temperature at which the prostate 14 has been brought by the microwaves emitted by the probe means 20. Such temperature data is of course important to determine the power instructions given by the control device 86 to the microwave generator M. W. G.

The tissues-protecting means according to the invention may comprise a part 90 fast with the rectal probe means 82, for protecting the rectal wall from high temperatures. According to a particularly advantageous embodiment, said screen-forming means 90 fast with the rectal wall from high temperatures. According to a particularly advantageous embodiment, said screen-forming means 90 fast with the rectal probe means comprise an rectal inflatable element 92 forming balloon fixed around the rectal probe 82 on its front end 82a which element is preferably supplied with an inflating liquid, advantageously a radioreflecting liquid medium 94, through a flexible tube 96 preferably identical to that used for inflating the urethral balloon 26 of the urethral probe means. Several temperature sensors 98 may be provided on the rectal probe or inside the balloon 92 for detecting the temperature at the level of the rectal wall 100 facing the prostate 14, the temperature data recorded by said sensors being transmitted to the thermometry device and to the central control device 86, such as a computer or the like.

In particular, said rectal temperature sensors can be used to measure the temperature reaching the rectal wall and to sense the probe of temperature and/or of microwave field generated by the microwaves as a means for detecting a correct position of the rectal probe and/or of the urethral probe.

According to a variant embodiment of the invention, said screen-forming means may comprise at least one wire, parallel to the mean electrical field, which wire is placed preferably in integral fashion with the rectal probe means 82 longitudinally thereto, in the direction of the emitting probe means 20.

Means may also be provided for protecting the sphincter 15 by a balloon system surrounding the probe means 20 similarly to balloon 26, which system can also be supplied by supply means 30.

It is obviously possible, according to the invention, to treat efficiently the prostate 14 by thermal effect, and in general to destroy tissues by thermal effect.

It is extremely easy with the echographic probe 82 connected with a screen-equipped echograph 84 to control the exact position of the emitting probe means 20 inside the prostate 14 by monitoring the echographic image of the emitting probe means 20 on the screen 84. When the practitioner sees that the emitting probe means is accurately positioned in the prostate 14, he can then trigger manually the control device 86 into operation, for carrying out the thermal effect treatment, the temperature being controlled inside the prostate 14 as well as in the surrounding tissues, and in particular in the rectum, by the various temperature sensors such as 98, 100.

It is also possible with the apparatus according to the invention, to protect efficiently the tissues other than the prostate, by various protection means 22, 90. Furthermore, the presence of the cooling means 32 prevents burn form occuring on the walls in contact with the probe means 20, particularly the walls of the urethra 34.

The invention also relates to a method for surgically treating tissues 12 by thermal effect, preferably the prostate 14, of the type using a microwave generating device 18 provided in an emitting probe means 20 capable of being introduced in a cavity of the body, wherein the sensitive tissues other than the tissues 12 to be treated are protected from the heat preferably by providing means forming radioreflecting screen 22, 90.

According to a variant embodiment of this surgical treatment method, said urethral emitting probe means 20 is inserted in the urethra very quickly up to a level for which the urethral balloon 26 which is of course deflated, reaches the bladder, then the urethral balloon 26 is inflated and a withdrawal movement of the urethral probe 20 is performed to lock the urethral probe 20 in the bladder neck.

It is preferably provided that one part 22 of said screen-forming means is placed at the level of an organ to be protected, such as the bladder 24 and/or the sphincter 15. This protection can be easily provided by filling the urethral ballon 26 with a cooling liquid and in particular an electroconductive liquid which provides radioreflection.

According to another advantageous variant of the method of the invention, the positioning of the urethral probe means 20 in relation to the prostate 14 is controlled by inserting a rectal probe means 82 in the rectum.

Advantageously, a protection forming radioreflecting means is also provided for protecting the rectal wall 100 from high temperatures.

This protection is ensured by the rectal balloon 92 inflated with a cooling liquid, in particular an electroconductive liquid.

The power of the microwave and/or the flow of the cooling liquid can be adjusted so as to maintain the urethral temperature below 44.5° C. and the rectal temperature below 42.5° C.

Other variant embodiments of the treatment method according to the invention follow from the description given hereinabove with reference to the apparatus.

By way of indication, the total duration of a treatment of the prostate by hyperthermia is normally about 1 hour. The emitting probe means will preferably emit microwaves at a frequency of about 1300 MHz±50 MHz and at a power which can be adjusted up to 50 W or even 100 W. The length of the actual emitting antenna is for example between 20 and 40 mm, these values being given by way of indication only. It is also possible to work at the old frequency of 915 MHz although this is less efficient than with the invention frequency of about 1300 MHz±50 MHz.

Obviously, the invention also extends to any means constituting technical equivalents of the means described herein, as well as to the combination thereof.

According to a specific embodiment, dilation means for temporary or intermittently increasing the outside diametre of the urethral probe are provided, said means being disposed relatively to the probe in such a manner as to enable the dilation of the urethral walls, at least at the level where the tissues are treated, and when so desired. In particular, said dilation means comprise at least one dilation balloon having means for filling and/or emptying the dilation balloon.

We claim:

1. A method for the surgical treatment of a patient having a prostate and a urethra in which the prostate is treated by thermal effect, comprising the steps of:

positioning a urethral emitting probe in the urethra, said probe having a front end, a rear end and an electromagnetic device for generating heat located in the vicinity of said front end and connected to an external means for generating electromagnetic energy;

inserting said urethral emitting probe into the urethra until said electromagnetic device reaches a part of the urethra located inside the prostate;

heat protecting at least the part of the urethra located inside the prostate from the heat produced by said electromagnetic device, when said electromagnetic device is activated;

activating said electromagnetic energy generating means for generating electromagnetic energy through said electromagnetic device towards the prostate at a frequency and a power effective to heat at least a portion of the prostate to a predetermined temperature range for a period of time sufficient to treat the prostate by thermal effect, while said protecting step minimizes damage to a urethral wall of the urethra by maintaining the part of the urethra in the prostate at a temperature, sufficiently less than the temperature to which at least the portion of the prostate is heated, to prevent thermal damage to the urethral wall.

2. The method of claim 1, wherein said probe has a longitudinal axis and wherein said heat protecting occurs by passing cooling fluid into said probe, through a first longitudinal chamber in said probe, through a second longitudinal chamber in said probe and then discharging said cooling fluid from said second longitudinal chamber, said first and second longitudinal chambers being parallel to the longitudinal axis of said probe, located along the electromagnetic device for generating heat, and being in communication with each other.

3. The method of claim 1, wherein said heat protecting step comprises passing cooling fluid through the front end of said probe.

4. A method for the surgical treatment of a patient having a urethra and a prostate including periurethral glands in which the periurethral glands are treated by thermal effect, comprising the steps of:

positioning a urethral emitting probe in the urethra, said probe having a front end, a rear end and an electromagnetic device for generating heat located in the vicinity of said front end and connected to an external means for generating electromagnetic energy;

inserting said urethral emitting probe into the urethra until said electromagnetic device reaches a part of the urethra located inside the prostate;

heat protecting at least said part of the urethra inside the prostate from the heat produced by said electromagnetic device to maintain said part of the urethra at a temperature value below a temperature providing thermal damage to the urethra;

activating said electromagnetic energy generating means for generating electromagnetic energy through said electromagnetic device towards the prostate at a frequency and a power effective to heat the periurethral glands located in the prostate to a predetermined temperature range for a period of time sufficient to provide necrosis of a localized zone of said periurethral glands by thermal effect while said heat protecting step impedes thermal damage to a urethral wall of the urethra by maintaining said part of the urethra in the prostate at a temperature sufficiently less than the temperature to which the periurethral glands are heated.

5. The method of claim 4, wherein said periurethral glands are heated to a temperature higher than about 45° C. and not more than 85° C. while maintaining the urethra at 44.5° C. or less.

6. The method of claim 4, wherein said activating step comprises heating the periurethral glands only by electromagnetic radiation emitted from within the urethra.

7. A method for the surgical treatment of a patient having a prostate and a urethra in which the prostate is treated by thermal effect, comprising the steps of:

positioning a urethral emitting probe in the urethra, said probe having a front end, a rear end and an electromagnetic device for generating heat located in the vicinity of said front end and connected to an external means for generating electromagnetic energy;

said urethral emitting probe comprising urethral thermal protecting means for thermally protecting at least a part of the urethra, said part of the urethra being inside the prostate, from the heat produced by said electromagnetic device;

activating said electromagnetic energy generating means for generating electromagnetic energy through said electromagnetic device towards the prostate at a frequency and a power effective to heat at least a portion of the prostate to a temperature higher than 45° C. and not more than 85° C. for a period of time sufficient to reach necrosis at a localized zone of the prostate by thermal effect, while said urethral thermal protecting means are activated to impede thermal damage to a urethral wall of the part of said urethra inside the prostate, by maintaining the part of the urethra in the prostate at a temperature, sufficiently less than the temperature to which at least the portion of the prostate is heated, to prevent thermal damage to the urethral wall.

8. The method of claim 7, wherein said activating step comprises heating the prostate only by electromagnetic radiation emitted from within said urethra.

9. A method for the surgical treatment of a patient having a prostate and a urethra in which the prostate is treated by thermal effect, comprising the steps of:

positioning a urethral emitting probe in the urethra, said probe having a front end, a rear end and an electromagnetic antenna means for generating heat located in the vicinity of said front end and connected to an external means for generating electromagnetic energy;

said urethral emitting probe comprising urethral heat protecting means extending along at least a part of said electromagnetic antenna means to protect at least a part of the urethra, said part of the urethra being inside the prostate, from the heat produced by said electromagnetic antenna means;

activating said electromagnetic energy generating means for generating electromagnetic energy through said electromagnetic antenna means towards the prostate at a frequency and a power effective to heat at least a portion of the prostate to a predetermined temperature range for a period of time sufficient to treat the prostate by thermal effect, while activating said urethral heat protecting means to impede thermal damage to a urethral wall of the part of the urethra inside the prostate by maintaining the part of the urethral wall in the prostate at a temperature, sufficiently less than the temperature to which at least the portion of the prostate is heated, to prevent thermal damage to the urethral wall.

10. The method of claim 9, wherein said electromagnetic antenna means is a microwave antenna located in the vicinity of said front end and connected to an external microwave generating device said method further comprising generating, with said external microwave generating device, said electromagnetic energy as microwave energy after said positioning step.

11. The method of claim 10, further comprising a step of heat protecting the urethra with said urethral heat protecting means by cooling the urethra between the microwave antenna and the prostrate.

12. The method of claim 9, wherein at least the portion of said prostate is heated to a temperature higher than about 45° C. and not more than 85° C. and the period of time is sufficient to reach necrosis at a localized zone of said prostate by thermal effect, while maintaining the urethra at 44.5° C. or less.

13. The method of claim 9, further comprising heating only by electromagnetic radiation emitted from within said urethra so as to reach necrosis at a localized zone of the prostate.

14. A method for the surgical treatment of a patient having a prostrate and a urethra in which the prostate is treated by thermal effect, comprising:

providing an emitting probe having a front end, said probe having an electromagnetic device for generating heat, said device being connected to a means for generating electromagnetic energy;

positioning said emitting probe for impacting the prostate with electromagnetic energy therefrom;

activating said electromagnetic energy generating means for generating electromagnetic energy through said electromagnetic device towards the prostate at a frequency and a power effective to heat an intermediate portion of the prostate to a temperature greater than 45° C., wherein a part of the urethra is within the prostate; and maintaining the part of the urethra in the prostate at a temperature, sufficiently less than the temperature to which the intermediate portion of the prostate is heated, to prevent thermal damage to a urethral wall of the part of the urethra within the prostate.

15. The method of claim 14, wherein said emitting probe is a urethral emitting probe, wherein said means for generating electromagnetic energy is external to said probe, and wherein said positioning step comprises inserting said urethral emitting probe into the urethra until said electromagnetic device reaches the level of the prostate.

16. The method of claim 15, further comprising the step of maintaining the temperature at the urethra, during said electromagnetic energy activating step, at 44.5° C. or less.

17. The method of claim 16, further comprising the step of maintaining the temperature at a rectal wall adjacent the prostate, during said electromagnetic energy activating step, at 42.5° C. or less.

18. The method of claim 14, wherein said activating step comprises activating said electromagnetic energy generating means for generating electromagnetic energy through said electromagnetic device towards said prostate at a frequency and a power effective to heat said prostate to a predetermined temperature of between 45° C. and 85° C.

19. The method of claim 14, further comprising the step of maintaining the temperature at the urethra, during said electromagnetic energy activating step, at 44.5° C. or less.

20. The method of claim 19, further comprising the step of maintaining the temperature at a rectal wall adjacent the prostate, during said electromagnetic energy activating step, at 42.5° C. or less.

21. The method of claim 14, wherein at least the portion of said prostate is heated to a temperature higher than about 45° C. and not more than 85° C. for a period of time sufficient to reach necrosis at a localized zone of said prostate by thermal effect, while maintaining the urethra at 44.5° C. or less.

22. The method of claim 14, wherein said activating step comprises heating the intermediate portion of the prostate only by electromagnetic radiation is emitted from within said urethra and said heating is sufficient to reach necrosis at a localized zone of the prostate.

23. The method of claim 14, wherein said probe has a longitudinal axis and wherein said heat protecting occurs by passing cooling fluid into said probe, through a first longitudinal chamber in said probe, through a second longitudinal chamber in said probe and then discharging said cooling fluid from said second longitudinal chamber, said first and second longitudinal chambers being parallel to the longitudinal axis of said probe, located along the electromagnetic device for generating heat, and being in communication with each other.

24. The method of claim 14, wherein said activating step comprises passing cooling fluid through the front end of said probe.

25. A method for the surgical treatment of a patient having a prostate and a urethra in which the prostate is treated by thermal effect, comprising the steps of:

positioning a urethral emitting probe in the urethra, said probe having a front end, a rear end and an electromagnetic device for generating heat located in the vicinity of said front end and connected to an external means for generating electromagnetic energy;

inserting said urethral emitting probe into the urethra until said electromagnetic device reaches a part of the urethra located inside the prostate;

heat protecting at least the part of the urethra located inside the prostate from the heat produced by said electromagnetic device, when said electromagnetic device is activated;

activating said electromagnetic energy generating means for generating electromagnetic energy through said electromagnetic device towards said prostate at a frequency and a power effective to heat at least a portion of said prostate to a predetermined temperature range for a period of time sufficient to treat said prostate by thermal effect, while said protecting step minimizes damage to a urethral wall of the urethra by maintaining the part of the urethra in said prostate at a temperature, sufficiently less than the temperature to which at least the portion of the prostate is heated, to prevent thermal damage to the urethral wall, wherein at least the portion of said prostate is heated to a temperature higher than about 45° C. and not more than 85° C. for a period of time sufficient to reach necrosis at a localized zone of said prostate by thermal effect, while maintaining the urethra at 44.5° C. or less.

26. A method for the surgical treatment of a patient having a prostate a bladder, and a urethra in which the prostate is treated by thermal effect, comprising the steps of:

positioning a urethral emitting probe in the urethra, said probe having a front end, a rear end and an electromagnetic device for generating heat located in the vicinity of said front end and connected to an external means for generating electromagnetic energy;

inserting said urethral emitting probe into the urethra until said electromagnetic device reaches a part of the urethra located inside the prostate;

heat protecting at least the part of the urethra located inside the prostate from the heat produced by said electromagnetic device, when said electromagnetic device is activated;

activating said electromagnetic energy generating means for generating electromagnetic energy through said electromagnetic device towards said prostate at a frequency and a power effective to heat at least a portion of said prostate to a predetermined temperature range for a period of time sufficient to reach necrosis at a localized zone of the prostate by thermal effect, while said protecting step minimizes damage to a urethral wall of the urethra by maintaining the part of the urethra in said prostate at a temperature, sufficiently less than the temperature to which at least a part of the prostate is heated, to prevent thermal damage to the urethral wail, wherein said prostate is heated only by electromagnetic radiation emitted from within said urethra.

27. The method of claim 26, further comprising maintaining a rectal wall adjacent the prostate at 42.5° C. or less.

28. A method for the surgical treatment of the prostate by thermal effect, comprising:

positioning a urethral emitting probe in the urethra, said probe having front end, a rear end and an electromagnetic device for generating heat located in the vicinity of said front end and connected to an external means for generating electromagnetic energy;

inserting said urethral emitting probe into the urethra until said electromagnetic device reaches a part of the urethra located inside the prostate;

heat protecting at least the part of the urethra located inside the prostate from the heat produced by said electromagnetic device, when said electromagnetic device is activated;

activating said electromagnetic energy generating means for generating electromagnetic energy through said electromagnetic device towards said prostate at a frequency and a power effective to heat at least a portion of said prostate to a predetermined temperature range for a period of time sufficient to reach necrosis at a localized zone of the prostate by thermal effect, while said protecting step minimizes damage to a urethral wall of the urethra by maintaining the part of the urethra in said prostate at a temperature, sufficiently less than the temperature to which at least a part of the prostate is heated, to prevent thermal damage to the urethral wall, wherein said prostate is heated only by electromagnetic radiation emitted from within said urethra, wherein said urethral emitting probe has an inflatable balloon located between the electromagnetic device for generating heat and the front end, and said inserting step comprises inserting said urethral emitting probe into the urethra with the balloon not inflated until said electromagnetic device reaches the part of the urethra located inside the prostate and the balloon reaches a bladder, and then inflating the ballon to lock the front end of the urethral probe in a neck of the bladder.

29. A method for the surgical treatment of the prostate by thermal effect, comprising:

positioning a urethral emitting probe in a urethra, said probe having a front end, a rear end and an electromagnetic device for generating heat located in the vicinity of said front end and connected to an external means for generating electromagnetic energy;

inserting said urethral emitting probe into the urethra until said electromagnetic device reaches a part of the urethra located inside the prostate;

heat protecting at least the part of the urethra located inside the prostate from the heat produced by said electromagnetic device, when said electromagnetic device is activated;

activating said electromagnetic energy generating means for generating electromagnetic energy through said electromagnetic device towards said prostate at a frequency and a power effective to heat at least a portion of said prostate to a predetermined temperature range for a period of time sufficient to reach necrosis at a localized zone of the prostate by thermal effect, while said protecting step minimizes damage to a urethral wall of the urethra by maintaining the part of the urethra in said prostate at a temperature, sufficiently less than the temperature to which at least a part of the prostate is heated, to prevent thermal damage to the urethral wall, wherein said heat protecting occurs by cooling the urethra between the electromagnetic device and prostate.

* * * * *